US006013461A

United States Patent [19]

Laken et al.

[11] Patent Number: 6,013,461

[45] Date of Patent: Jan. 11, 2000

[54] APC MUTATION ASSOCIATED WITH FAMILIAL COLORECTAL CANCER IN ASHKENAZI JEWS

[75] Inventors: Steve Laken, Baltimore, Md.; Stephen Gruber, Ann Arbor, Mich.; Gloria Petersen, Glen Arm, Md.; Kenneth Kinzler, Belair, Md.; Bert Vogelstein, Baltimore, Md.

[73] Assignee: The Johns Hopkins University, Baltimore, Md.

[21] Appl. No.: 09/023,673

[22] Filed: Feb. 13, 1998

Related U.S. Application Data

[62] Division of application No. 08/791,883, Jan. 31, 1997, Pat. No. 5,879,890.

[51] Int. Cl.[7] .......................... G01N 33/53; C07K 15/28; C07K 5/00

[52] U.S. Cl. ............................... 435/7.1; 435/6; 436/500; 530/350; 530/387.1; 530/388.1

[58] Field of Search ..................... 435/6, 7.1; 530/387.1, 530/388.1, 350; 436/500

[56] References Cited

U.S. PATENT DOCUMENTS

| | | | |
|---|---|---|---|
| 5,879,890 | 3/1999 | Laken et al. ............................... | 435/6 |

FOREIGN PATENT DOCUMENTS

| | | |
|---|---|---|
| WO 92 13103 | 8/1992 | WIPO . |
| WO 94 21814 | 9/1994 | WIPO . |
| WO 95 17523 | 6/1995 | WIPO . |

OTHER PUBLICATIONS

Laken, S.J., et al.: "Familial colorectal cancer in Ashkenazim due to a hypermutable tract in APC" Nature Gentics, vol. 17, No. 1, 1997, pp. 79–83.

Petrukhin, L., et al.: "The 11307K APC mutation does not predispose to colorectal cancer in Jewish ashkenazi breast and breast–ovarian cancer in kindredss" Cancer Research, vol. 57, 1997, pp. 5480–5484.

Gryfe, R., et al. Hypermutability of the APC 11370K polymorphism in Ashenaszi Jewish colorectal cancer.

Kinzler, et al., *Cell* 87:159–170 (1996).

Groden, et al., *Cell* 66:589–600 (1991).

Nishisho, et al., *Science* 253:665–669 (1991).

Leach, et al., *Cell* 75:1215–1225 (1993).

Liu, et al., *Nature Medicine* 2:169–174 (1996).

Fishel, et al., *Cell* 75:1027–1038 (1993).

Papadopoulos et al., *Science* 263:1625–1629 (1994).

Nicolaides et al., *Nature* 371:75–80 (1994).

Powell, et al., *New England Journal of Medicine* 329(27):1982–1987 (1993).

Rubinfeld et al., *Science* 262:1731–1734 (1993).

Su et al., *Science* 262:1734–1737 (1993).

Morin et al., *Proc. Natl. Acad. Sci. USA* 93:7950–7954 (1996).

Friedl et al., *Hum. Genet.* 97:579–584 (1996).

Smith et al., *Proc. Natl. Acad. Sci. USA* 90:2846–2850 (1993).

Papadopoulos et al., *Nature Genetics* 11:99–102 (1995).

Thibodeau, et al., *Science* 260:816–819 (1993).

Parsons et al., *Cancer Research* 55:5548–5550 (1995).

Aaltonen, et al., *Science* 260:812–816 (1993).

*Primary Examiner*—Jeffrey Fredman

*Attorney, Agent, or Firm*—Banner & Witcoff, Ltd.

[57] ABSTRACT

During routine screening of a patient with a family history of colorectal cancer for truncating APC mutations, a novel missense mutation was identified. Upon further evaluation, it was found that 6% of Ashkenazi Jews carry this mutation, and that it was present in ~20% of Ashkenazis with a family history of CRC. Probes, methods, and kits for identifying individuals affected with this missense mutation are provided.

6 Claims, 3 Drawing Sheets

Segment 3 Full Length →

Truncated Segment 3 →

N N N N N N M N N

97 —
69 —
46 —
30 —
21.5 —

APC MUTATION ASSOCIATED WITH FAMILIAL COLORECTAL CANCER IN ASHKENAZI JEWS

This application is a divisional of application Ser. No. 08/791,883, filed Jan. 31, 19997, which is now U.S. Pat. No. 5,879,890.

The U.S. government retains certain rights in the invention because it supported the inventors under NIH grants CA 43460 and CA 62924.

TECHNICAL FIELD OF THE INVENTION

This invention is related to detection of a gene predisposing carriers to colorectal cancer.

BACKGROUND OF THE INVENTION

Of the 160,000 new cases of colorectal cancer (CRC) diagnosed each year in the U.S., at least 15% have a hereditary component. Two well-defined syndromes, Familial Adenomatous Polyposis (FAP) and Hereditary Non-Polyposis Colorectal Cancer (HNPCC), account for up to 5% of the familial cases. Truncating APC mutations are responsible for FAP, and defective mismatch repair genes cause HNPCC. However, the genes responsible for the majority of the familial cases are unknown. There is a need in the art for additional tools and information for identifying familial cancer genes.

SUMMARY OF THE INVENTION

It is an object of the present invention to provide an allele-specific nucleic acid probe.

It is another object of the present invention to provide methods of determining the presence of a mutation in an APC gene.

It is an object of the present invention to provide a kit useful for determining a mutation in an APC gene.

These and other objects of the invention are achieved by providing an allele-specific nucleic acid probe comprising the nucleic acid sequence of a region of a human mutant APC or its ribonucleotide equivalent, wherein said region contains a T to A transversion at nucleotide 3920.

In another embodiment of the invention a method is provided for determining the presence in a proband of a mutation in APC which is associated with a family history of colorectal cancer among Ashkenazi Jews. The method comprises the step of:

determining the presence of a T to A transversion mutation at nucleotide 3920 in an APC gene of a proband.

According to another embodiment of the invention another method is provided for determining the presence in a proband of a mutation in APC which is associated with a family history of colorectal cancer among Ashkenazi Jews. The method comprises the step of:

determining the presence of a lysine at amino acid 1307 of APC protein of the proband.

In yet another embodiment of the invention a third method is provided of determining the presence in a proband of a mutation in APC which is associated with a family history of colorectal cancer among Ashkenazi Jews. The method comprises the step of:

determining the presence of a lysine codon at codon 1307 of an APC gene of the proband.

In still another embodiment of the invention a kit is provided for detecting a mutation in APC which predisposes carriers to colorectal cancer. The kit comprises:

a pair of oligonucleotide primers for amplifying at least a portion of APC exon 15 comprising nucleotide 3920; and an allele-specific probe comprising the nucleic acid sequence of a region of a human mutant APC or its ribonucleotide equivalent, wherein said region contains a T to A transversion at nucleotide 3920.

These and other embodiments of the invention which will be apparent to those of skill in the art upon reading this disclosure, provide the art with tools and methods for rapidly and easily detecting a particular allele which is associated with familial colorectal cancer.

BRIEF DESCRIPTION OF THE DRAWINGS

FIG. 1 *a*. Lanes marked "N" contain polypeptides from patients without the I1307K mutation and lane "M" contains polypeptides from the index patient heterozygous for the I1307K mutation. The arrow points to the doublet of truncated polypeptides present in the patient with the mutation. The reason for the doublet at the indicated position is not clear, but could represent two independent slippage events at the $(A)_8$ tract.

DETAILED DESCRIPTION

Figure 1A:
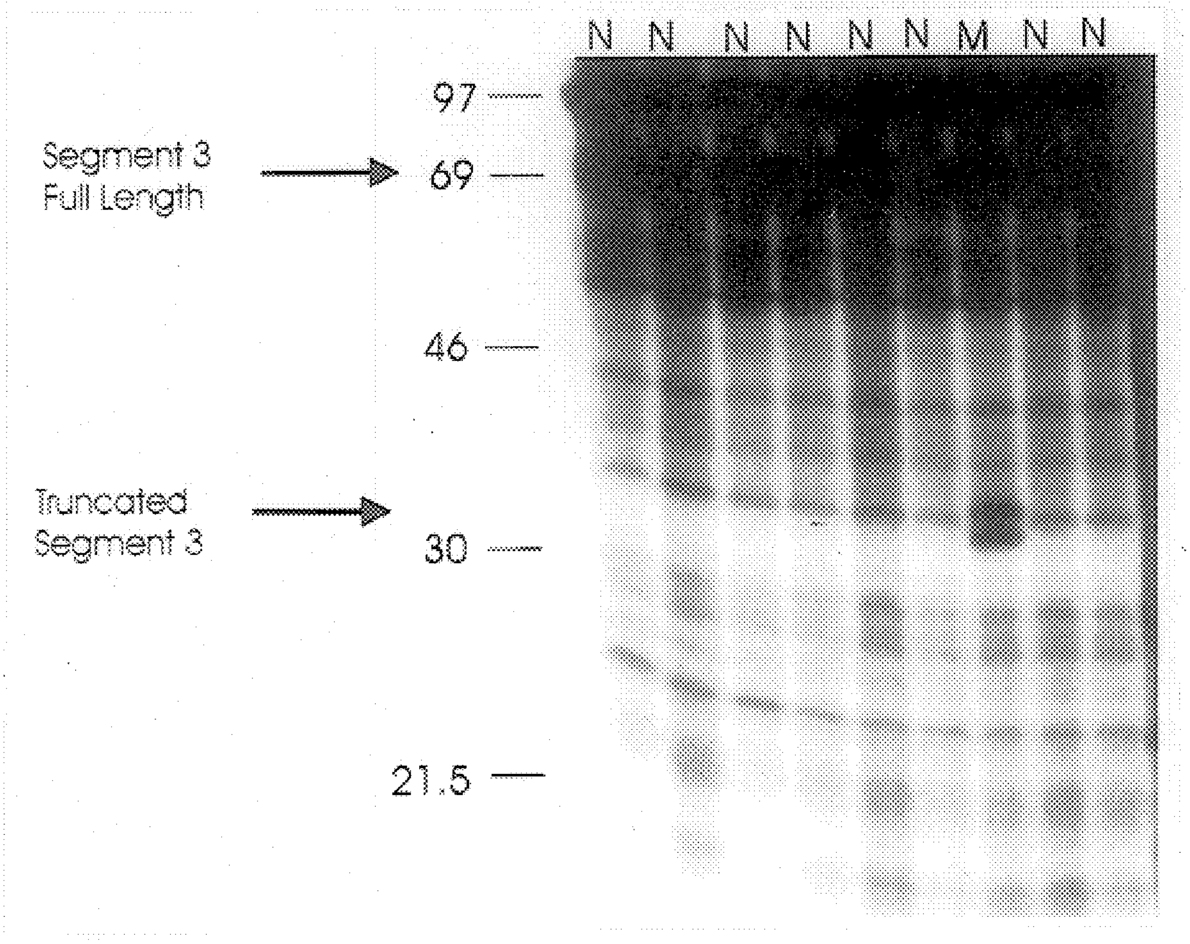
FIG. 1 IVSP assays of APC codons 1099 to 1693.
FIG. 1*b*. Sequence of PCR products from the index patient. The wild-type sequence is AAA ATA AAA and the mutant sequence is AAA AAA AAA, predicted to substitute a lysine for isoleucine at codon 1307. The arrow points to the heterozygous mutation site.

It is a discovery of the present inventors that a particular missense mutation in the APC gene is prevalent in the Ashkenazi Jewish population. This mutation is associated with familial colorectal cancer. In addition, it appears to be associated with a different set of symptoms than is caused by the well-known truncating mutations in APC. Rather than causing the thousands of polyps often found in typical FAP patients, this mutation appears to cause "attenuated polyposis", i.e., a much lower frequency of polyps.

The mutation causes an isoleucine to lysine substitution in amino acid 1307 of APC. This has been found to be caused by a T to A transversion mutation at nucleotide 3920. Allele-specific oligonucleotides containing a portion of the APC gene containing this mutation can be used to detect those who carry the mutation in the population in general or in the Ashkenazi population, or in families having colorectal cancers in the Ashkenazi population. The oligonucleotides can be used as probes for hybridization. They can be used as primers, e.g., for allele-specific PCR. They can also be used to generate immunogenic polypeptides or fusion proteins for use in generating specific antibodies which recognize the mutant epitope.

In order to determine whether a particular individual (a proband) has the mutation, either his DNA, RNA, or proteins can be examined for evidence of the mutation. If the nucleic acids are examined, one would ascertain the presence of a mutation causing a lysine at amino acid 1307. If the proteins are examined, the presence of the lysine can be determined directly in the proteins by sequencing or by using specific immunological reagents, such as monoclonal antibodies or monospecific polyclonal antibodies which recognize the mutant epitope but not the wild-type form of the APC protein. Similarly, the nucleic acids can be sequenced to determine the presence of the mutation. Any single or combination of techniques can be used for detecting mutations. For example, RNA can be reverse transcribed and in vitro expressed, and the in vitro synthesized protein can be analyzed by any means known in the art. Alternatively, RNA can be reverse transcribed into DNA, the DNA amplified using PCR, and the PCR products probed with an allele-specific probe.

A kit useful for using such a technique is also provided. It contains primers for amplifying exon 15 (all or at least the part which includes codon 1307) as well as an allele-specific probe, according to the invention. Other optional components of the kit include written instructions, a DNA polymerase for performing PCR, buffers, probes for detecting other mutations in APC, reverse transcriptase, reaction vessels, membranes for hybridizations.

The evidence that the I1307K mutation is disease-causing is three-fold. First, the mutation occurs in a “gate-keeping” gene critical for suppressing the initiation of the neoplastic process, and in a region of APC thought to be essential for its proper function. Second, the frequency of the mutation is markedly higher in index cases of familial colorectal cancer patients than in the general Ashkenazi population. And third, within such families, the mutation was found in all but one of 11 patients with colorectal neoplasia. This mutation certainly does not confer the thousands of polyps often found in typical FAP patients with truncating mutations in the middle third of the APC coding region. The phenotype more closely resembles that of patients with “attenuated polyposis” due to truncating mutations in the amino-terminus of APC. It will be intriguing to determine, in larger future studies, whether the presence of I1307K is sufficient to confer CRC predisposition, or whether other genetic or environmental factors combine with I1307K to cause such a predisposition.

Figure 2:
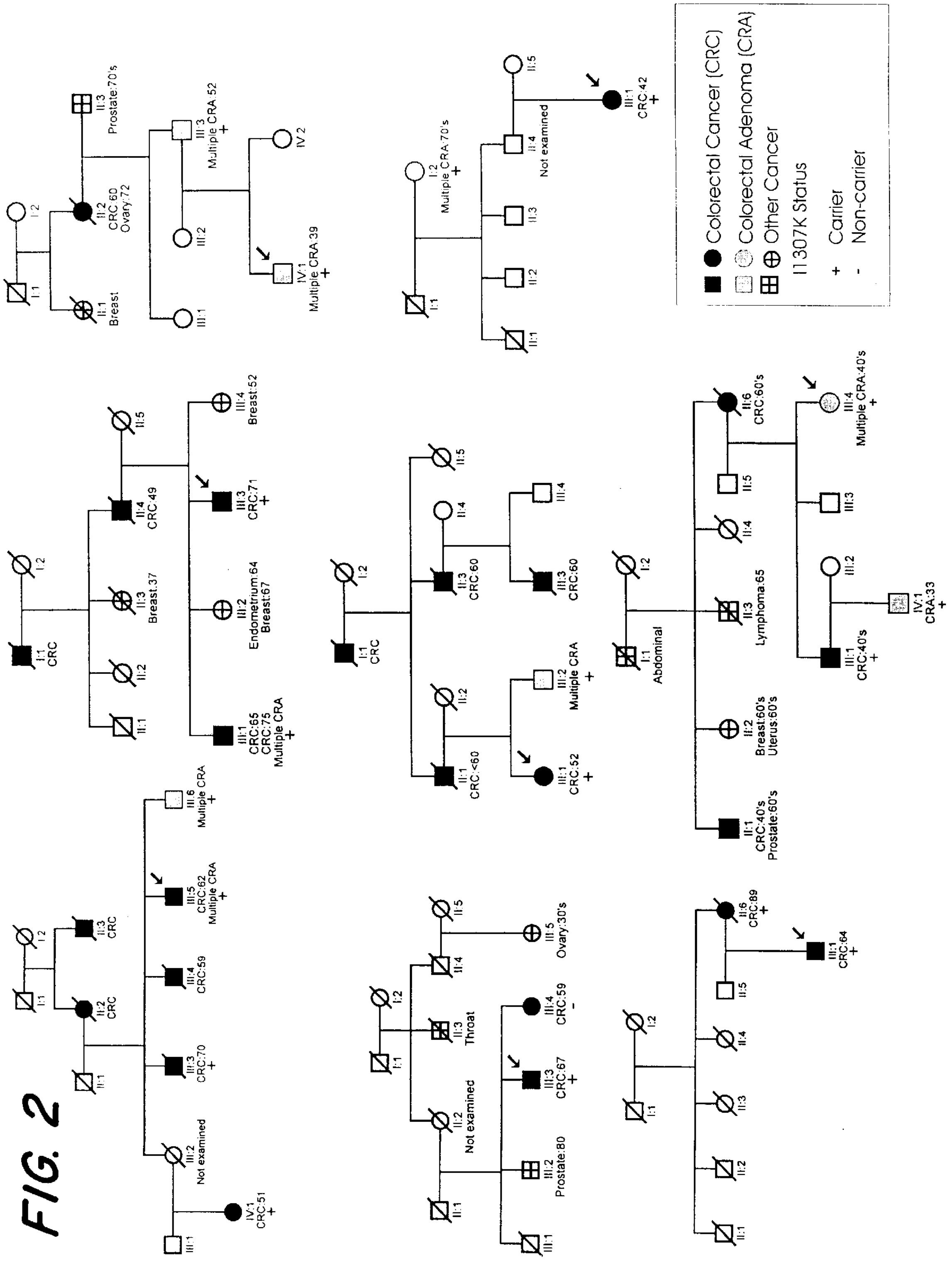
FIG. 2 Pedigrees of probands with the I1307K mutation. Patients affected with CRC are denoted by filled symbols, patients with polyps are denoted by shaded boxes, and patients with other cancers are denoted by crosses. Cancer types and age at diagnosis are indicated when known. Individuals with the I1307K mutation are denoted as "+", and individuals who were tested for this mutation but found not to carry it are indicated as "–".

These results therefore have substantial implications for colorectal cancer predisposition in the Ashkenazi population. Previous studies have demonstrated that other mutations, including those predisposing to breast cancer, can be found at elevated frequency in this population, though not as commonly as I1307K (Nature Medicine 2(11)1179–1183) (Cancer Research 56(15) 3409–3414). As yet, our results should not prompt generalized screening of Ashkenazis for I1307K, as the relative risk of cancer associated with this mutation, in the absence of a family history of CRC, has not yet been established. However, in families in which two or more individuals have CR neoplasia, our results suggest that individuals with I1307K are at high risk of colorectal cancer (at least 30% lifetime risk, judged from the pedigrees shown in FIG. 2 and conservative assumptions). As effective measures are available for limiting CRC morbidity through genetic testing in appropriately selected families, further evaluation of this issue seems warranted. Finally, it will be of interest to determine whether additional missense mutations of APC might contribute to familial colorectal cancer in other populations.

The above disclosure generally describes the present invention. A more complete understanding can be obtained by reference to the following specific examples which are provided herein for purposes of illustration only, and are not intended to limit the scope of the invention.

EXAMPLE 1

This example describes the discovery of the I1307K missense mutation in APC.

Figure 1B:
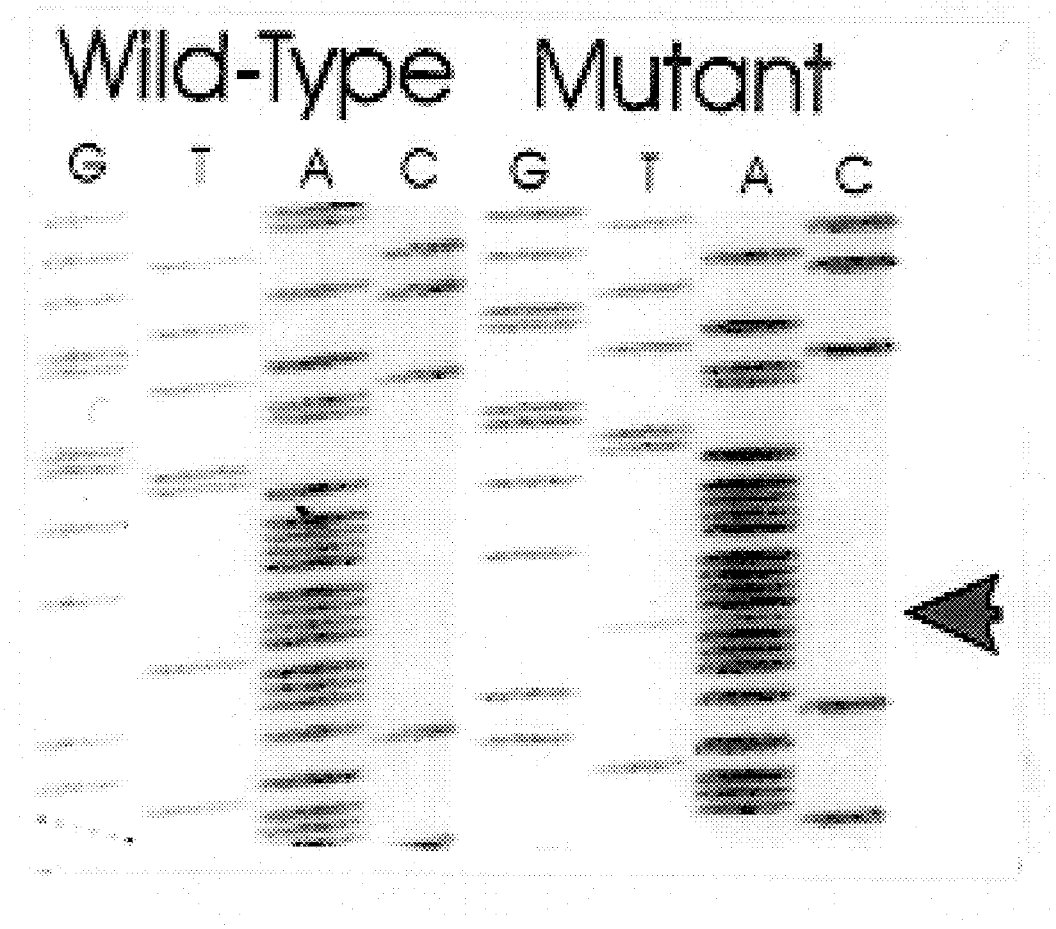

APC gene testing of FAP patients is routinely performed using the in vitro synthesized protein assay (IVSP). This test is performed by PCR-amplifying a segment of DNA with a 5' primer that contains sites for T7 transcription and mammalian translation. Following transcription and translation of the PCR products, the polypeptides are separated by electrophoresis. During such a screen, a 39 year old patient with multiple colorectal adenomas (CRA) was found to have a truncated protein predicted to lie between codons 1099 and 1693 in exon 15 (FIG. 1*a*). Surprisingly, sequencing of the relevant region of APC from this patient revealed no truncating mutations, but instead a single alteration, consisting of a T to A transversion at nucleotide 3920, was identified. This mutation resulted in a substitution of lysine for isoleucine at codon 1307, in the region of APC (residues 1020–2075) responsible for binding to β-catenin (FIG. 1*b*). A variety of experiments, including IVSP assays on cloned PCR products, showed that the truncation was an in vitro phenomenon caused by the T to A substitution mutation, and that no truncated APC proteins were found in the patient’s lymphocytes.

Methods

IVSP. IVSP was performed essentially as described in Powell et al. The PCR products containing codon 1307 were amplified with primers 5' gga gga tcc tgt agg aat ggt atc tcg-3' and 5'-gga tcc taa tac gac tca cta tag gga gac cac cat ggt ttc tcc ata cag gtc acg g-3' (obtained from DNAgency, Malvern, Pa.). They were transcribed and translated in vitro, using reagents available from Promega (Madison, Wis.). The PCR products were purified from agarose gels and cloned into the pZero vector (Clontech, Palo Alto, Calif.). Clones were sequenced using Thermo Sequinase (Amersham, Arlington Heights, Ill.). PCR products from the clones were then used as templates for IVSP reactions.

EXAMPLE 2

This example demonstrates that the truncation observed in vitro was presumably due to “slippage” of one of the enzymes used for IVSP at the $(A)_8$ tract created by the mutation.

To determine whether the I1307K mutation was responsible for the truncated protein found in the IVSP assay, the PCR products were cloned into *E. coli*. Clones which contained either the wild-type sequence or the mutated sequence were isolated and used for IVSP analysis. The cloned mutant sequence produced both the truncated protein and the full length protein in a ratio of ~1:3. These results clearly show that a missense mutation can produce a truncated protein when evaluated in vitro.

To determine whether a truncated protein was produced from the I1307K mutation in vivo, protein extracts from the patient’s lymphoblastoid cells were immunoblotted using an antibody directed against the amino-terminus of APC; no truncated APC protein was detected. To increase the sensitivity of immunoblotting, we employed MAMA (mono-allelic mutation analysis). The index patient’s lymphoblastoid cells were fused with hamster cells, and hybrids containing a single human chromosome 5 were isolated. This made it possible to evaluate the gene products from the I1307K allele in the absence of the wt allele; still only full length protein was detected (data not shown).

We also considered the possibility that the $(A)_8$ tract resulting from the I1307K mutation (FIG. 1*b*) might create an unstable homopolymeric sequence which could be mutated in vivo through polymerase "slippage". This would cause a frameshift through an insertion or deletion of an A residue within the $(A)_8$ tract. To test this hypothesis, a paraffin-embedded colorectal tumor from this patient was microdissected to isolate neoplastic cells from surrounding normal tissue. Purified DNA from these cells was used to amplify the region containing the mutation. No insertions or deletions in the I1307K tract were detected (data not shown). In addition, other microsatellites from the patient's tumor were tested (see Methods), and the absence of instability in these sequences made it unlikely that this patient had HNPCC.

Methods

Isolation of DNA from paraffin-embedded tumors. DNA was isolated from slides containing paraffin-embedded colorectal adenoma of the index patient as described previously (Jen, NEJM, 1993). To evaluate the stability of the $(A)_8$ repeat embodying the I1307K mutation, the following primers were used: 5'-agc tga cct agt tcc aat c-3' and 5'-cag ctg aag atg aaa tag ga- 3'. To evaluate microsatellite instability at other loci, the primers and conditions described in Liu et al, Nature Medicine, 1996, were used. MAMA. Lymphoblastoid cells from the index case were fused with hamster UCW-56 cells using a BTX electroporation. Following selection for retention of human chromosome 5, isolated clones were selected and evaluated by PCR for the I1307K mutation (as described above) to determine which of the two alleles was retained. Clones containing each allele were used for immunoblot analyses, using antibodies and conditions previously described.

EXAMPLE 3

This example demonstrates the biological significance of the mutation by examining its occurrence in populations of individuals.

To evaluate the biological significance of this presumptive missense mutation, several analyses were performed. First, an allele-specific oligonucleotide (ASO) hybridization assay was designed to determine the population frequency of I1307K (see Methods). As the patient was a member of a partially inbred group (Ashkenazi Jew), we examined both non-Ashkenazis and Ashkenazi population. I1307K was not found in any of 243 non-Ashkenazis tested, but a remarkably high proportion of Ashkenazis (6.1%) were found to carry the alteration (Table 1). The difference in I1370K prevalence between Ashkenazis and non-Ashkenazis was highly significant ($p<0.0001$ by $\chi^2$ test).

To determine whether the I1307K mutation was associated with CRC in the Ashkenazi population, we examined 212 Ashkenazis with CRC. Using the ASO, it was found that 10.8% of such patients harbored the I1307K mutant. In each of these cases, sequencing was used to verify the ASO results. This elevated frequency was consistent with the possibility that the I1307K was associated with CRC predisposition, and the difference between Ashkenazis with CRC and the general Ashkenazi population was statistically significant ($p<0.02$ by $\chi^2$ test). To further explore the relationship between CRC and I1307K, the CRC patients were segregated according to family history. Forty of the 212 probands had a first degree relative with colorectal neoplasia (either cancer or benign tumor [polyp]). In the remaining 172 probands, either no first degree relatives had colorectal neoplasia or the family history was unknown (n=172). Twenty percent of probands from the 40 familial cases carried the I1307K. mutation, a frequency that was highly significant when compared either to the 6.1% found in the general Ashkenazi population or the 8.7% found in CRC patients without a known family history of CR neoplasia (Table 1).

TABLE 1

| Series | I1307K + | Total | % |
|---|---|---|---|
| Normal Controls | | | |
| Non-Ashkenazi | 0 | 243 | 0%[a] |
| Ashkenazi | 47 | 766 | 6.1%[b] |
| Ashkenazi Colorectal Cancer Patients | | | |
| Total | 23 | 212 | 10.8%[c] |
| With Family History of CR Neoplasia | 8 | 40 | 20.0%[d] |
| No Known History of CR Neoplasia | 15 | 172 | 8.7%[e] |

a vs. b, $p < 0.0001$ by $\chi^2$
b vs c, $p < 0.02$ by $\chi^2$
b vs. d, $p < 0.01$ by $\chi^2$
c vs. e, $p < 0.05$ by $\chi^2$ Methods Patient selection. Randomly selected Ashkenazis taken from a group undergoing testing for Tay-Sachs diseases were used as the control Ashkenazi group. Non-Ashkenazis consisted of another randomly selected group of non-Jewish individuals who had contributed blood samples for diverse reasons. Two groups of Ashkenazi colorectal cancer patients were analyzed. One group represented a consecutive series of individuals who been treated for colorectal cancer at Memorial Sloan-Kettering. The second consisted of a group of individuals who had been evaluated for CRC at the Johns Hopkins Hospital. This second group was not a consecutive series, and was heavily biased towards patients with a family history of CRC.

Mutation analyses. Genomic DNA was used as template for PCR with the following primers: 5'-gatgaaataggatgtaatcagacg and 5'-cttcgctcacaggatcttcagc. The PCR product was slot-blotted onto nylon filters and hybridized with oligonucleotides corresponding to the wt or mutant sequence at codon 1307 (5'-aatagcagaaataaaagaaaagat or 5'-aaatagcagaaaaaaagaaaagat, respectively). Hybridizations were performed at room temperature for 1 hour, then washed for 30 minutes in 2×SSC, 0.1% SDS at room temperature followed by a 2 minute wash at 56° C. in 2×SSC, 0.1% SDS. To confirm the blotting results, the PCR products exhibiting mutations were sequenced with Thermo Sequenase, using the following primer: 5'-gatgaaataggatgtaatcagacg. In two patients with the I1307K mutation, PCR products encompassing the entire coding region of APC were obtained from DNA or cDNA as described previously and directly sequenced.

EXAMPLE 4

This example demonstrates an additional test of the association between the I1307K mutation and disease.

We examined its segregation in cancer families. We were able to identify 8 families in which at least two first degree relatives had colorectal neoplasia (cancer or polyps) and in which the proband carried the I1307K alteration. Eleven relatives affected with CRC or CRA were examined using the ASO, and ten were found to carry the I1307K mutant (FIG. 2); each was confirmed by sequencing. This result was very unlikely due to chance alone ($p<0.01$, Bayesian probability).

Although these data strongly suggested that the I1307K mutation was intrinsically related to CRC predisposition, it remained possible that this mutation was in linkage disequilibrium with another mutation in APC. To rule this out, sequencing of the "hot-spot" region of APC was performed on two individuals with familial CRC and the I1307K mutation. Only one previously identified, silent polymorphism was found, making it unlikely that another APC mutation in the sequenced region was segregating with disease.

REFERENCES

1. Kinzler, et al., *Cell* 87:159–170 (1996)
2. Groden, et al., *Cell* 66:589–600 (1991)
3. Nishisho, et al., *Science* 253:665–669 (1991)
4. Leach, et al., *Cell* 75:1215–1225 (1993)
5. Liu, et al., *Nature Medicine* 2:169–174 (1996)
6. Fishel, et al., *Cell* 75:1027–1038 (1993)
7. Papadopoulos et al., *Science* 263:1625–1629 (1994)
8. Nicolaides et al., *Nature* 371:75–80 (1994)
9. Powell, et al., *New England Journal of Medicine* 329(27):1982–1987 (1993)
10. Rubinfeld et al., *Science* 262:1731–1734 (1993)
11. Su et al., *Science* 262:1734–1737 (1993)
12. Morin et al., *Proc. Natl. Acad. Sci. USA* 93:7950–7954 (1996)
13. Friedl et al., *Hum. Genet.* 97:579–584 (1996)
14. Smith et al., *Proc. Natl. Acad. Sci. USA* 90:2846–2850 (1993)
15. Papadopoulos et al., *Nature Genetics* 11:99–102 (1995)
16. Thibodeau, et al., *Science* 260:816–819 (1993)
17. Parsons et al., *Cancer Research* 55:5548–5550 (1995)
18. Aaltonen, et al., *Science* 260:812–816 (1993)

---

We claim:

1. A method of determining the presence in a proband of a mutation in APC which is associated with a family history of colorectal cancer among Ashkenazi Jews, the method comprising the step of:

determining the presence of a lysine at amino acid 1307 of APC protein of the proband.

2. The method of claim 1 wherein an antibody which binds specifically to an APC epitope comprising the I1307K mutation is contacted with an APC protein-containing sample of the proband.

3. The method of claim 1 wherein an APC protein isolated from the proband or produced using an APC nucleic acid isolated from the proband is subjected to amino acid sequencing.

4. An immunological reagent comprising antibodies for detecting the presence of a mutation in an APC allele which is associated with a family history of colorectal cancer among Ashkenazi Jews, wherein the immunological reagent recognizes an epitope of a mutant APC protein having a lysine residue at amino acid 1307 but does not recognize an APC protein having an isoleucine residue at amino acid 1307.

5. The immunological reagent of claim 4 wherein the antibodies are monoclonal antibodies.

6. The immunological reagent of claim 4 wherein the antibodies are monospecific polyclonal antibodies.

* * * * *

```
SEQUENCE LISTING


(1) GENERAL INFORMATION:

   (iii) NUMBER OF SEQUENCES: 11


(2) INFORMATION FOR SEQ ID NO:1:

     (i) SEQUENCE CHARACTERISTICS:
          (A) LENGTH: 9 base pairs
          (B) TYPE: nucleic acid
          (C) STRANDEDNESS: single
          (D) TOPOLOGY: linear

    (xi) SEQUENCE DESCRIPTION: SEQ ID NO:1:

AAAATAAAA                                                          9


(2) INFORMATION FOR SEQ ID NO:2:

     (i) SEQUENCE CHARACTERISTICS:
          (A) LENGTH: 9 base pairs
          (B) TYPE: nucleic acid
          (C) STRANDEDNESS: single
          (D) TOPOLOGY: linear

    (xi) SEQUENCE DESCRIPTION: SEQ ID NO:2:

AAAAAAAAA                                                          9


(2) INFORMATION FOR SEQ ID NO:3:

     (i) SEQUENCE CHARACTERISTICS:
          (A) LENGTH: 27 base pairs
          (B) TYPE: nucleic acid
          (C) STRANDEDNESS: single
          (D) TOPOLOGY: linear

    (xi) SEQUENCE DESCRIPTION: SEQ ID NO:3:

GGAGGATCCT GTAGGAATGG TATCTCG                                     27


(2) INFORMATION FOR SEQ ID NO:4:

     (i) SEQUENCE CHARACTERISTICS:
          (A) LENGTH: 58 base pairs
          (B) TYPE: nucleic acid
          (C) STRANDEDNESS: single
          (D) TOPOLOGY: linear

    (xi) SEQUENCE DESCRIPTION: SEQ ID NO:4:

GGATCCTAAT ACGACTCACT ATAGGGAGAC CACCATGGTT TCTCCATACA GGTCACGG   58
```

-continued (2) INFORMATION FOR SEQ ID NO:5:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:5:

AGCTGACCTA GTTCCAATC 19

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:6:

CAGCTGAAGA TGAAATAGGA 20

(2) INFORMATION FOR SEQ ID NO:7:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:7:

GATGAAATAG GATGTAATCA GACG 24

(2) INFORMATION FOR SEQ ID NO:8:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:8:

CTTCGCTCAC AGGATCTTCA GC 22

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:9:

AATAGCAGAA ATAAAAGAAA AGAT 24

(2) INFORMATION FOR SEQ ID NO:10:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:10:

AAATAGCAGA AAAAAAAGAA AAGAT 25

(2) INFORMATION FOR SEQ ID NO:11:

-continued (i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:11:

GATGAAATAG GATGTAATCA GACG 24